US012622763B2

(12) United States Patent
Porter et al.

(10) Patent No.: US 12,622,763 B2
(45) Date of Patent: May 12, 2026

(54) STERILE COVER ASSEMBLY

(71) Applicant: ACIST Medical Systems, Inc., Eden Prairie, MN (US)

(72) Inventors: Blaise D. Porter, Minneapolis, MN (US); Thomas Bergner, Bloomington, MN (US); Spencer Fodness-Bondhus, Columbia Heights, MN (US)

(*) Notice: Subject to any disclaimer, the term of this patent is extended or adjusted under 35 U.S.C. 154(b) by 290 days.

(21) Appl. No.: 17/010,345

(22) Filed: Sep. 2, 2020

(65) Prior Publication Data

US 2022/0061947 A1 Mar. 3, 2022

(51) Int. Cl.
*A61B 50/00* (2016.01)
*G06F 1/16* (2006.01)

(52) U.S. Cl.
CPC ........ *A61B 50/00* (2016.02); *A61B 2050/005* (2016.02); *G06F 1/1607* (2013.01); *G06F 1/1679* (2013.01)

(58) Field of Classification Search
CPC ... A61B 46/10; A61B 2050/005; A61B 46/50; A61B 46/40; A61B 2017/0046; G06F 1/1607; G06F 1/1628; G06F 1/1633; G06F 1/1656; G06F 1/1679; G06F 2200/1633; G02B 27/0006; A45C 2011/001;

(Continued)

(56) References Cited

U.S. PATENT DOCUMENTS

| | | | | |
|---|---|---|---|---|
| 1,535,312 A | * | 4/1925 | Thomas | G03B 17/02 396/27 |
| 5,812,188 A | * | 9/1998 | Adair | A61B 1/00048 600/101 |

(Continued)

FOREIGN PATENT DOCUMENTS

| | | | | |
|---|---|---|---|---|
| DE | 102012213322 A1 | * | 1/2014 | ............. A61B 46/10 |
| WO | 2017062466 A2 | | 4/2017 | |

OTHER PUBLICATIONS

PCT Partial International Search Report and Written Opinion dated Dec. 6, 2021 for related International Application No. PCT/US2021/047301, 8 pages.

(Continued)

*Primary Examiner* — Allen L Parker
*Assistant Examiner* — Gage Crum
(74) *Attorney, Agent, or Firm* — Carlson, Caspers, Vandenburgh & Lindquist, P.A.

(57) ABSTRACT

A touchscreen cover assembly embodiment is configured to create a sterile interface between a touchscreen and a user and includes a sterile frame and a sterile cover member. The sterile frame includes a forward frame surface and a rearward frame surface opposite the forward frame surface. The sterile frame defines an interior opening, and the sterile frame is configured to be secured to the touchscreen such that the rearward frame surface faces the touchscreen and the interior opening is aligned with a user interface of the touchscreen. The sterile cover member includes a forward cover portion and a rearward cover portion. The sterile cover member is configured to be secured to the touchscreen by the sterile frame such that the forward cover portion is positioned between the interior opening and the user interface of the touchscreen and the rearward cover portion is positioned over a housing of the touchscreen.

17 Claims, 12 Drawing Sheets

(58) Field of Classification Search
CPC ......... A45C 2011/002; A45C 2011/003; A45F
2200/0508; A45F 2200/0516; A45F
2200/0525; H04B 1/3888; H04B
2001/3894; H05K 5/0217; H05K 5/023;
H04M 1/17; C09J 7/40; B29C 63/02;
B29C 63/0056; B32B 27/08; F21V 21/40;
F21V 21/403
USPC .................................................. 361/679.26
See application file for complete search history.

(56) References Cited

U.S. PATENT DOCUMENTS

| | | | | |
|---|---|---|---|---|
| 6,151,083 | A * | 11/2000 | Hung ..................... | G06F 1/1609 348/832 |
| 6,377,320 | B1 * | 4/2002 | Ananian .................. | H04N 5/65 348/E5.131 |
| 8,164,886 | B1 * | 4/2012 | Shelander ............. | G06F 1/1601 250/221 |
| 8,885,110 | B1 * | 11/2014 | St. Clair .................. | H04N 5/65 348/836 |
| 9,019,691 | B1 * | 4/2015 | Matsuoka ............. | G06F 1/1616 361/679.01 |
| 9,930,795 | B2 * | 3/2018 | Chang ................... | G06F 1/1613 |
| 2004/0194673 | A1 * | 10/2004 | Comeaux ............. | A47G 11/004 108/90 |
| 2006/0006678 | A1 * | 1/2006 | Herron, Jr. ............ | E05B 1/0069 292/336.3 |
| 2006/0096225 | A1 * | 5/2006 | Root ........................ | F16M 1/00 52/582.1 |
| 2006/0230576 | A1 * | 10/2006 | Meine .................... | A47K 17/00 16/110.1 |
| 2007/0139874 | A1 * | 6/2007 | Tanaka .................. | G06F 1/1656 361/679.59 |
| 2010/0053085 | A1 | 3/2010 | Hall | |
| 2012/0167347 | A1 * | 7/2012 | Bigajer ................... | B25G 1/00 16/422 |
| 2012/0170211 | A1 * | 7/2012 | Waller .................... | A45F 5/102 361/679.56 |
| 2013/0048203 | A1 * | 2/2013 | Yau ........................... | B32B 7/06 428/41.5 |
| 2013/0186798 | A1 | 7/2013 | Naor | |
| 2014/0150211 | A1 * | 6/2014 | Bracey .................. | E05B 1/0069 16/110.1 |
| 2014/0247489 | A1 * | 9/2014 | Wilson ...................... | B32B 7/12 156/60 |
| 2014/0338676 | A1 * | 11/2014 | Marinchak ............. | A61B 46/10 128/855 |
| 2016/0089858 | A1 * | 3/2016 | Swanson ................. | B32B 27/18 156/247 |
| 2017/0075442 | A1 * | 3/2017 | Thomas .................. | G06F 3/041 |
| 2017/0242455 | A1 | 8/2017 | Dickens | |
| 2017/0266929 | A1 * | 9/2017 | Wilson ...................... | B32B 7/12 |
| 2019/0094914 | A1 * | 3/2019 | Wilson .................. | G06F 3/0412 |
| 2021/0092262 | A1 * | 3/2021 | Marchione ............ | G06F 1/1626 |

OTHER PUBLICATIONS

English language translation of DE 10 2012 213 322 A1, prepared by RWS Translations Ltd., (translated Apr. 24, 2024).

* cited by examiner

STERILE COVER ASSEMBLY

TECHNICAL FIELD

This disclosure generally relates to systems, assemblies, and methods for creating a sterile interface. Certain embodiments relate to systems, assemblies, and methods including a touchscreen cover assembly for creating a sterile interface between a user and a touchscreen.

BACKGROUND

A sterile environment may be desirable in a variety of contexts, including in the medical context. In the medical context, various medical procedures may require a sterile environment in order to reduce the risk of infection and/or cross contamination to an exposed patient. To help facilitate a sterile environment, medical personnel present in the vicinity of the medical procedure sanitize themselves and wear protective clothing, such as disposable gloves, gowns, and aprons. To further help facilitate a sterile environment, many devices used for a medical procedure may be single use devices. However, for certain devices useful in a medical procedure it is impractical, for instance due to cost considerations, to dispose of such devices after a single use. Yet, these reusable devices should not comprise the sterile environment.

SUMMARY

Draping can be used in an attempt to shield certain reusable devices and, thereby, attempt to prevent such reusable devices from compromising the sterile environment. However, such draping can have drawbacks as it may not have the ability to fit the device adequately. For example, this can result in portions of the device being exposed within the sterile environment. As another example, the draping's inability to provide an adequate fit at the device can be undesirable for devices that require medical personnel interaction. For instance, this draping may be relatively loose fitting at the device's user interface thereby making it difficult for a medical user in the sterile environment to provide certain input at the user interface.

Certain devices may include a touchscreen at which particular multi-touch inputs, such as touch-and-drag inputs, are needed from the medical user to provide necessary commands to the device. However, the presence of the loose fitting drape over the touchscreen may make it difficult, and in some cases even prevent, the medical user from successfully providing such multi-touch inputs at the touchscreen. This is of particular note in the medial procedure context where quick and accurate inputs can be important. Yet, since it is impractical to have a single use touchscreen, to create and maintain a sterile environment it is desirable to shield as much of the touchscreen as possible, including the user interface.

Embodiments disclosed herein include touchscreen cover assemblies and methods that can create and/or maintain a sterile interface between a touchscreen and a user. Various such embodiments can be configured to fit a touchscreen device in a manner that reduces, or eliminates, exposed portions of the touchscreen device in the sterile environment. These embodiments can also be configured to fit a touchscreen device in a manner that better facilitates successful user input at the touchscreen's user interface. For example, these embodiments can be configured to facilitate various multi-touch inputs, such as touch-and-drag inputs, that are needed from a medical user in order to provide necessary commands to the device. This can be particularly useful in the medial procedure context as it can allow for such necessary inputs at the user interface in a quick and accurate manner while also creating and/or maintaining a sterile environment between the touchscreen and the medical user.

One exemplary embodiment includes a touchscreen cover assembly. This touchscreen cover assembly embodiment is configured to create a sterile interface between a touchscreen and a user. The touchscreen cover assembly includes a sterile frame and a sterile cover member. The sterile frame includes a forward frame surface and a rearward frame surface opposite the forward frame surface. The sterile frame defines an interior opening, and the sterile frame is configured to be secured to the touchscreen such that the rearward frame surface faces the touchscreen and the interior opening is aligned with a user interface of the touchscreen. The sterile cover member includes a forward cover portion and a rearward cover portion. The sterile cover member is configured to be secured to the touchscreen by the sterile frame such that the forward cover portion is positioned between the interior opening and the user interface of the touchscreen and the rearward cover portion is positioned over a housing of the touchscreen.

In a further embodiment of the touchscreen cover assembly, the sterile cover member is configured to be secured to the touchscreen by the sterile frame such that the rearward cover portion is positioned over the housing of the touchscreen. The rearward cover portion can be positioned over the housing of the touchscreen at a surface of the touchscreen different than a surface of the touchscreen having the user interface. Positioning the rearward cover portion over the housing can include positioning the rearward cover portion over one or more surfaces of the touchscreen that are perpendicular to and/or opposite to the surface of the touchscreen having the user interface while the forward cover portion is positioned between the interior opening of the sterile frame and the user interface of the touchscreen.

As such, certain touchscreen cover assembly embodiments can create and/or maintain a sterile interface between the user and the touchscreen, including the touchscreen's user interface as well as ancillary components of the touchscreen, such as its mounting mechanism, connected cabling, and/or control lines.

Another exemplary touchscreen cover assembly embodiment includes multiple sterile cover members. For example, such a touchscreen cover assembly can be configured to create a sterile interface between a touchscreen and a user and the touchscreen cover assembly can include a first sterile cover member and a second sterile cover member removably adhered to the first sterile cover member. The first sterile cover member can include a first cover member rear surface and a first cover member forward surface opposite the first cover member rear surface. The first cover member rear surface can include a first adhesive that is configured to removably adhere the first sterile cover member to the touchscreen. The second sterile cover member can include a second cover member rear surface and a second cover member forward surface opposite the second cover member rear surface. The second cover member rear surface can include a second adhesive removably adhering the second sterile cover member to the first cover member forward surface. The first adhesive and the second adhesive can be configured to allow the second sterile cover member to be removed from the first sterile cover member while adhering the first sterile cover member to the touchscreen.

In a further embodiment of the touchscreen cover assembly, the first sterile cover member can include a first tab extending out from the first sterile cover member at a first region of the assembly. And, the second sterile cover member can include a second tab extending out from the second sterile cover member at a second region of the assembly spaced apart from the first region. These first and second tabs can be configured to be gripped by a user to allow the user to pull the second sterile cover member off of the first sterile cover member so that the second sterile cover member can be disposed of while the first sterile cover member is configured to remain adhered to the touchscreen. This can be useful in conveniently using the touchscreen cover assembly across multiple medical procedures while maintaining the sterile interface between the touchscreen and the user.

An additional exemplary embodiment includes a sterile packaging. The sterile packaging can define an interior volume within which an embodiment of a touchscreen cover assembly can be sealed. The touchscreen cover assembly sealed within the interior volume of the sterile packaging can be any embodiment of a touchscreen cover assembly disclosed herein. The touchscreen cover assembly sealed within the interior volume of the sterile packaging can be sterilized prior to placement within the packaging and maintain its sterility by sealing it within the packaging. In this way, a sterile user can unseal the packaging, remove the touchscreen cover assembly, and secure the touchscreen cover assembly for use at the touchscreen.

A further exemplary embodiment includes a method of packaging a touchscreen cover assembly configured to create a sterile interface between a touchscreen and a user. The packaged touchscreen cover assembly can be any embodiment of a touchscreen cover assembly disclosed herein. The method can include sterilizing the touchscreen cover assembly and placing the touchscreen cover assembly into a sterile packaging. The method can also include sealing the sterile packaging with the touchscreen cover assembly inside.

Another exemplary embodiment includes a method for using a touchscreen cover assembly that is configured to create a sterile interface between a touchscreen and a user. The touchscreen cover assembly that is used can be any embodiment of a touchscreen cover assembly disclosed herein The method can include removing the touchscreen cover assembly from sealed sterile packaging and securing the touchscreen cover assembly onto a touchscreen. For instance, in this method, the touchscreen cover assembly can be secured onto the touchscreen by securing the sterile frame at the touchscreen such that the forward cover portion is positioned between the sterile frame's interior opening and the user interface of the touchscreen and the rearward cover portion is positioned over the touchscreen's housing.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are intended for use in conjunction with the explanations in the following description and are not necessarily not scale. Embodiments of the invention will hereinafter be described in conjunction with the appended drawings, wherein like numerals denote like elements.

FIG. 1 shows an embodiment of a touchscreen cover assembly secured to a touchscreen of the medical device.

FIG. 2A shows this touchscreen cover assembly unsecured to a touchscreen while FIG. 2B shows this touchscreen cover assembly secured to the touchscreen.

FIG. 3 shows a sterile cover member of the touchscreen cover assembly covering a housing of the touchscreen as well as a mounting mechanism for the touchscreen.

FIG. 4A is a side elevational view of the sterile frame, FIG. 4B is a close-up, side elevational view of a portion of the sterile frame of FIG. 4A, and FIG. 4C is a close-up, perspective view of a portion of the sterile frame of FIG. 4A with a handle of the sterile frame being secured to a touchscreen.

FIG. 6 shows the embodiment of the touchscreen including multiple sterile cover members covering a housing of the touchscreen as well as a mounting mechanism for the touchscreen.

FIG. 7A is a plan view of the touchscreen cover assembly embodiment having multiple sterile cover members each with a tab. FIG. 7B is a plan view of the touchscreen cover assembly embodiment after a first sterile cover member, present in FIG. 7A, has been removed to reveal a second sterile cover member. And, FIG. 7C is a plan view of the touchscreen cover assembly embodiment after the second sterile cover member, present in FIG. 7B, has been removed to reveal a third sterile cover member.

DETAILED DESCRIPTION

Figure 1:
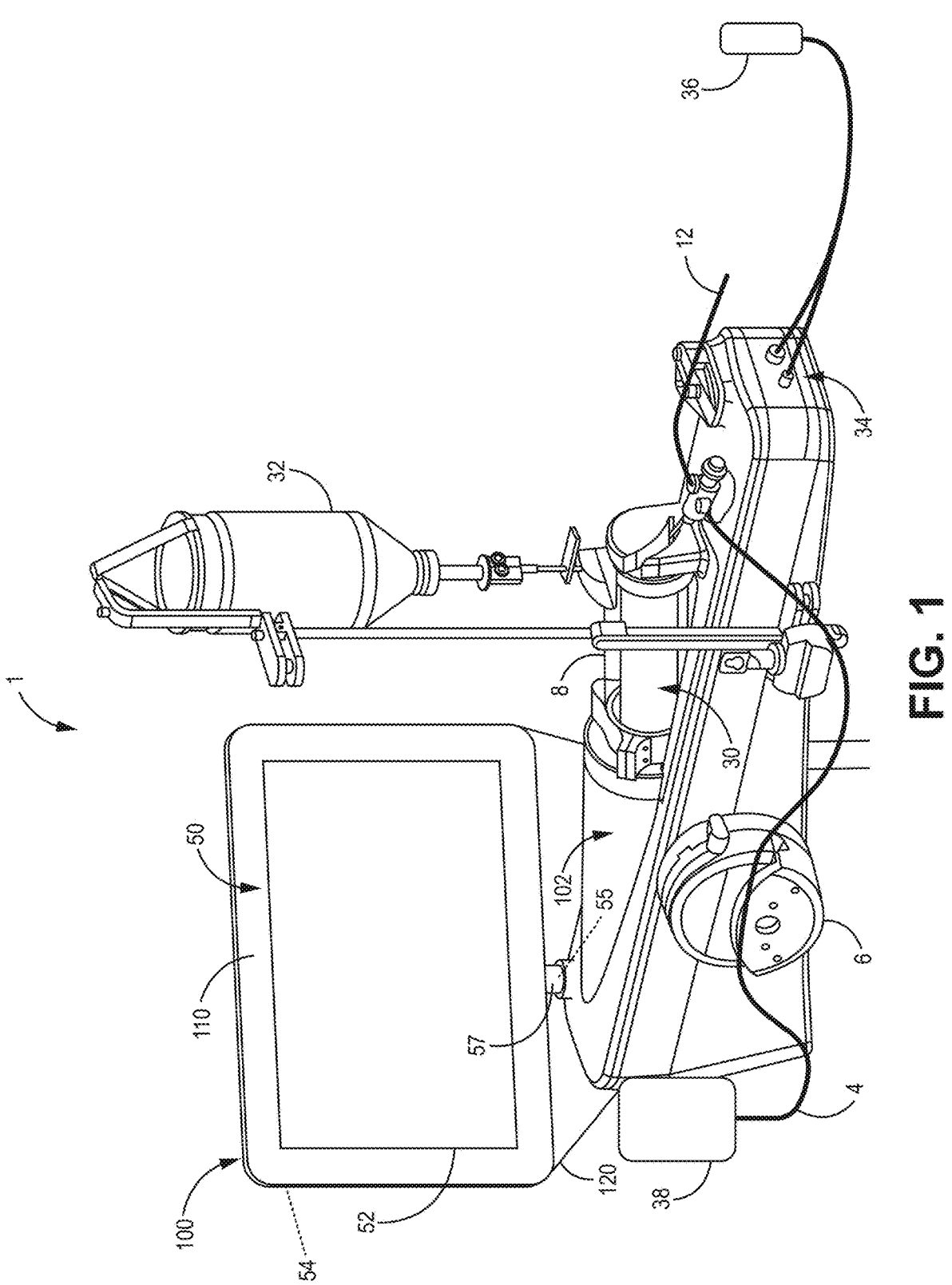
FIG. 1 is a perspective view of an embodiment of a medical device in a sterile environment.

The following detailed description is exemplary in nature and provides some practical illustrations and examples. Those skilled in the art will recognize that many of the noted examples have a variety of suitable alternatives. A number of various exemplary systems, assemblies, and methods are disclosed herein using the description provided as follows in addition to the accompanying drawings. Each of the systems, assemblies, and methods disclosed herein can be employed independently or in combination with one or more (e.g., all) of the other systems, assemblies, and methods disclosed herein. Like reference numerals are used in this description and in the drawings to convey like elements.

FIG. 1 shows a perspective view of an embodiment of a medical device 1 in a sterile environment. The medical device 1, as shown in FIG. 1, includes an embodiment of a touchscreen cover assembly 100 secured to a touchscreen 50 of the medical device 1.

In the illustrated example, the medical device 1 is a powered fluid injection system. The powered fluid injection system 1 can be used to inject a quantity of fluid into a vessel via a catheter assembly. The fluid injected by the powered fluid injection system 1 can be, for example, a contrast fluid, non-contrast fluid (e.g., saline), or a combination contrast and non-contrast fluid. Exemplary medical procedures performed in connection with the powered fluid injection system 1 can include OCT imaging, IVUS imaging, angiographic procedures, and other forms of diagnostic imaging procedures.

The powered fluid injection system 1 can hold one or more fluid containers with fluid to be introduced into the patient during a procedure. For example, fluid in a container 32, such as contrast fluid, can be drawn into a reservoir 8 by retracting a drive ram and plunger 30 during operation of the powered fluid injection system 1. This contrast fluid can then be pressurized (e.g., 1,000-1,300 psi) and delivered to the patient by moving the drive ram and plunger 30 forward within the reservoir 8. The drive ram and plunger 30 can receive operative force from an injector head 4 that houses a motor of other operative power source. As another example, fluid in a container 38, such as a non-contrast fluid (e.g., a flushing fluid, such as saline), can be pressurized and delivered to the patient by the pump 6 (e.g., a peristaltic pump). Each of the contrast fluid and the non-contrast fluid can be conveyed along patient tubing 12 and introduced into the patient via a catheter at the patient.

In some embodiments, the powered fluid injection system 1 can include a hand-control device 36 to help control certain operational aspects of the powered fluid injection system 1. The hand-control device 36 can be coupled to the touchscreen 50 via a control line 34. A user can manipulate the hand-control device 36 to control injection of fluid from the powered fluid injection system 1. For example, the user can use the hand-control device 36 to start and stop a fluid injection. In many cases, the operational aspects of the system 1 that can be controlled by the hand-control device 36 are limited to a small subset of basic commands.

The touchscreen 50 can be used to provide a larger range of commands. For instance, a user can use the touchscreen 50 of the powered fluid injection system 1 to set up various parameters and/or injection protocols for a given fluid injection procedure. For instance, the user can interact with the touchscreen 50, which can function as a control panel for the powered fluid injection system 1, to input injection protocols such as flow rate, injection volume, injection duration and/or other injection parameters. In one embodiment, the touchscreen 50 includes a user interface 52, enabling a user to view and modify injection parameters as desired. The touchscreen 50 can also be used to initialize the powered fluid injection system 1 (e.g., to prepare it for a patient fluid injection), or to activate certain features or sequences of operations of the powered fluid injection system 1. The touchscreen 50 can be controlled by one or more processors, which may also control other components of the powered fluid injection system 1

Because injection procedures using the powered fluid injection system 1 are generally performed on an exposed patient, it is desirable to create and maintain a sterile environment at the area in which the injection procedure is performed. This includes a user of the powered fluid injection system 1 generally sterilizing himself/herself prior to entering the environment as well as creating and maintaining sterility of devices in the procedure environment, including the powered fluid injection system 1. To help maintain sterility, certain components of the system 1, such as the hand-control device 36 and tubing 12, can be single or limited use components. However, other components, such as the touchscreen 50, are used across a large number of procedures performed on different patients. For this reason, it is desirable to create and maintain sterility at the touchscreen 50 of the powered fluid injection system 1 in a manner that allows the touchscreen 50 to be continually used in subsequent procedures on various patients.

In the illustrated embodiment of the system 1, a touchscreen cover assembly 100 can be used to facilitate the sterile environment at the touchscreen 50. The touchscreen cover assembly 100 can be configured to create a sterile interface between the touchscreen 50 and the user. In this way, the user can interact with the touchscreen 50 to carry out the injection procedure using the system 1 without compromising the user's sterility when interacting with the touchscreen 50.

As shown in FIG. 1, the touchscreen cover assembly 100 can include a sterile frame 110 and a sterile cover member 120. The sterile frame 110 can be configured to secure the touchscreen cover assembly 100 to the touchscreen 50. When the touchscreen cover assembly 100 is secured to the touchscreen 50, the sterile cover member 120 can cover the touchscreen 50, including the user interface 52 and a housing 54 of the touchscreen 50. In addition to covering the touchscreen 50, the touchscreen cover assembly 100 can cover other portions of the powered fluid injection system 1 (including one or more (e.g., each) of control lines 34, connected cabling 55, a mounting mechanism 57, or the like). As a user interacts with the touchscreen 50 to provide input to the powered fluid injection system 1 via the user interface 52, the touchscreen cover assembly 100 can accommodate a variety of gestures, including multi-touch gestures, such as drag-and-swipe inputs and rotational inputs, without compromising the user's sterility. In some cases, the touchscreen cover assembly 100 can be positioned such that use of interactive connected components, such as the hand-control device 36 (as further discussed below), does not compromise the sterile interface created by the touchscreen cover assembly 100.

Figure 2B:
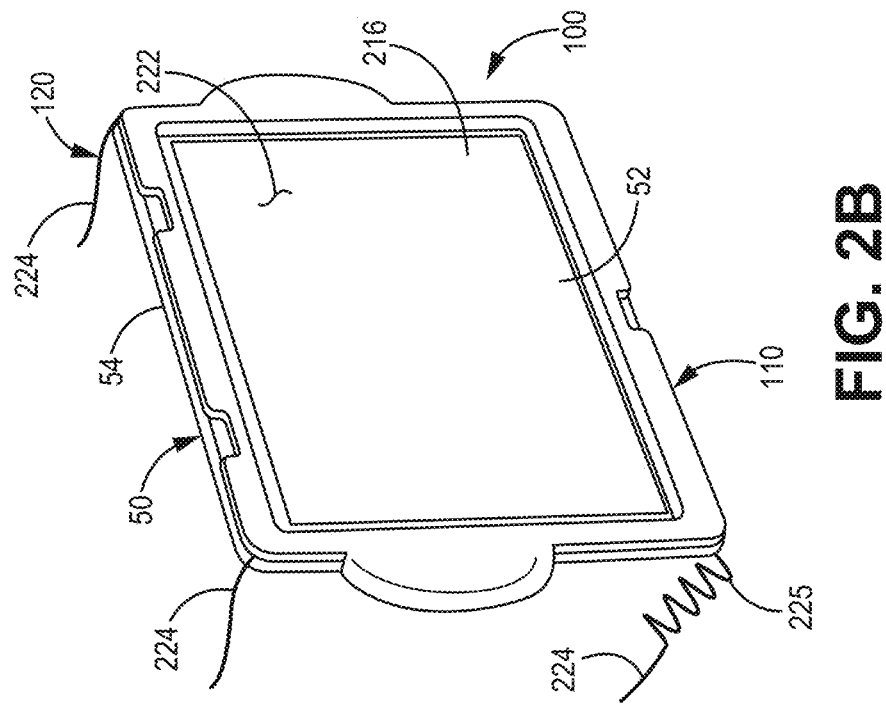
FIGS. 2A and 2B are perspective views of the touchscreen cover assembly of FIG. 1.
Figure 2A:
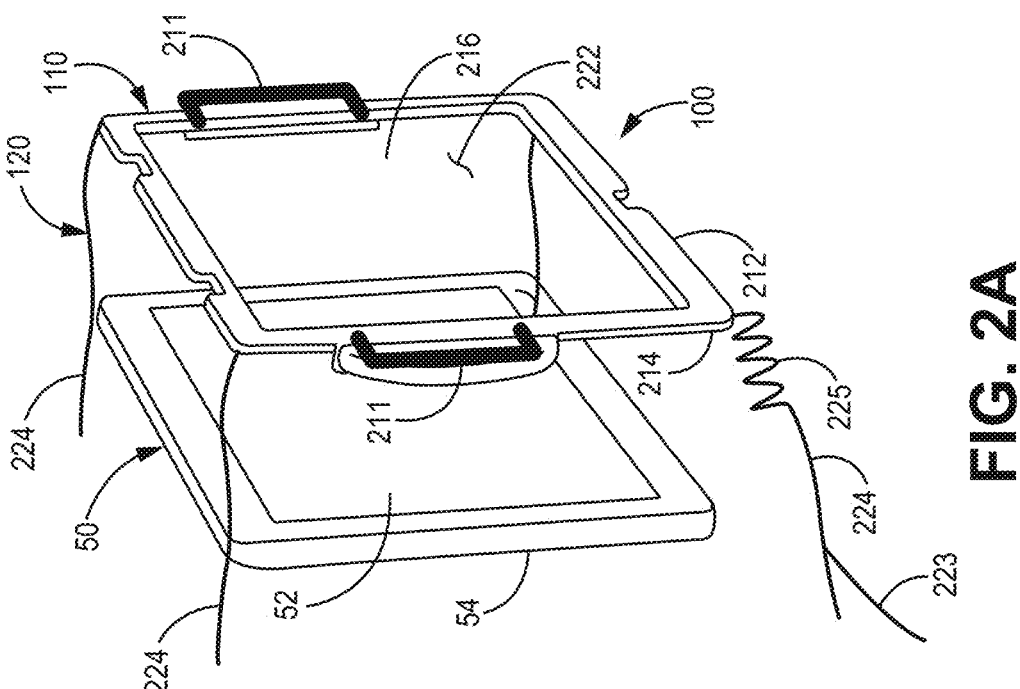

FIGS. 2A and 2B show perspective views of the touchscreen cover assembly 100. FIG. 2A shows this touchscreen cover assembly 100 unsecured to the touchscreen 50 while FIG. 2B shows the touchscreen cover assembly 100 secured to the touchscreen 50. The touchscreen cover assembly 100 can be configured to create a sterile interface between the touchscreen 50 and the user of the touchscreen 50 in the sterile medical procedure environment.

The touchscreen cover assembly 100 can include the sterile frame 110 and the sterile cover member 120. The sterile cover member 120 can be configured to be secured to the touchscreen 50 by the sterile frame 110. The sterile frame 110 can include a forward frame surface 212 and a rearward frame surface 214 that is opposite the forward frame surface 212. The sterile frame 110 can define an interior opening 216. This interior opening can extend from the forward frame surface 212 to the rearward frame surface 214. The sterile cover member 120 can include a forward cover portion 222 and a rearward cover portion 224. The sterile frame 110 can be configured to be secured to the touchscreen 50 such that the rearward frame surface 214 faces the touchscreen 50 (e.g., the user interface 52) and the interior opening 216 is aligned with the user interface 52 of the touchscreen 50.

The touchscreen cover assembly 100 can include one or more features to facilitate sterile frame 110 and sterile cover member 120 handling and positioning onto the touchscreen 50 by a nonsterile user. For example, the cover assembly 100 can include one or more removable handling interfaces 211, 223. In the illustrated embodiment of FIG. 2A, the cover assembly 100 includes two removable handling interfaces 211 (e.g., in the form of tabs) at the sterile frame 110 and one removable handling interface 223 (e.g., in the form of a pull string) at the sterile cover member 120. In other embodiments, various numbers of handling interfaces can be present at the assembly 100 as suitable for the particular application. The handling interfaces 211, 223 can be used by a nonsterile user as contact points to position the assembly 100 at the touchscreen 50. For instance, the handling interfaces 211 can be used as contact points for the nonsterile user to place the sterile frame 110 at the touchscreen 50 and the handling interface 223 can be used as a contact point for the nonsterile user to place the sterile cover member 120 over the housing 54 of the touchscreen 50. Once the assembly 100 is appropriately positioned at the touchscreen 50, the handling interfaces 211, 223 can be removed from the assembly 100, as shown in FIG. 2B. In this way, the handling interfaces 211, 223 can serve as a contact point for a nonsterile user so as to preserve sterility of the sterile frame 110 and sterile cover member 120.

When secured to the touchscreen 50 with the sterile frame 110, the sterile cover member 120 can be configured to be positioned to cover the touchscreen 50. For instance, the sterile cover member 120 can be configured to cover a majority, or in some cases all, of the touchscreen 50. The touchscreen 50 can include a number of surfaces. At one surface of the touchscreen 50 (e.g., a "front" surface of the touchscreen 50), the user interface 52 can be included. Another surface of the touchscreen 50 can include a housing 54. For instance, as shown in FIG. 2A, the surface of the touchscreen 50 that includes the housing 54 can be a surface opposite the surface of the touchscreen 50 that includes the user interface 52. As shown in FIG. 2B, the sterile cover member 120 can be configured to be secured to the touchscreen 50 by the sterile frame 110 such that the forward cover portion 222 is positioned between the interior opening 216, of the sterile frame 110, and the user interface 52, of the touchscreen 50. And, as also shown in FIG. 2B, the sterile cover member 120 can be configured to be secured to the touchscreen 50 by the sterile frame 110 such that the rearward cover portion 224 is positioned over the housing 54 of the touchscreen 50. As such, in this embodiment, the sterile cover member 120 is configured to be secured to the touchscreen 50 by the sterile frame 110 such that the rearward cover portion 224 is positioned over the housing 54 of the touchscreen 50 at an opposite surface (e.g., a "rear" surface) of the touchscreen than a surface of the touchscreen 50 having the user interface 52 (e.g., a "front" surface).

In some embodiments, the rearward cover portion 224 can include one or more fitting adjustment members 225. The embodiment illustrated in FIGS. 2A and 2B includes one fitting adjustment member 225, but other embodiments can include more than one fitting adjustment member 225 (e.g., four fitting adjustment members 225 spaced apart from one another about the rearward cover portion 224 each adjacent to one of each of the four corners of the touchscreen 50). The fitting adjustment member 225 can provide a degree of slack in the rearward cover portion 224. As such, the fitting adjustment member 225 can be configured to move between a rearward cover portion retracted position, in which the slack in the rearward cover portion 224 is brought together at the fitting adjustment member 225, and a rearward cover portion extended position, in which the slack in the rearward cover portion 224 is pulled out to increase the length of the rearward cover portion 224. In some examples, the fitting adjustment member 225 can be biased to the rearward cover portion retracted position, as shown in FIGS. 2A and 2B. In these examples, application of a force at the rearward cover portion 224 overcomes the bias at the fitting adjustment member 225 to bring the fitting adjustment member 225 to the rearward cover portion extended position. Such a configuration can help to facilitate a desired fit of the rearward cover portion 224 at the housing 54 of the touchscreen 50.

Depending on the embodiment, the sterile cover member 120 can be formed by a single component enclosure or a combination of two or more components together forming an enclosure. In one embodiment, the sterile cover member 120 can be a single component enclosure that forms both the forward cover portion 222 and the rearward cover portion 224. As such, in this embodiment the forward cover portion 222 and the rearward cover portion 224 can be integrated to form a single piece sterile cover member such that the forward cover portion 222 and the rearward cover portion 224 can be a continuous piece from end to end. In such an embodiment, the sterile frame 110 can be configured to hold the forward cover portion 222 of the sterile cover member 120 tightly across the user interface 52 of the touchscreen 50 in a manner that eliminates cover member that would materially impact the ability of a user to input multi-gesture commands at the user interface 52. In another embodiment, the sterile cover member 120 can be a combination of one component forming the rearward cover portion 224 and another component forming the forward cover portion 222. For instance, in such embodiment, the forward cover portion 222 can be formed by a planar cover sheet extending in a plane across the interior opening 216 of the sterile frame 110. In one example, such a planar cover sheet forward cover portion 222 can be integral to the sterile frame 110 while another component forming the rearward cover portion 224 can be positioned and then secured in place by placement of the sterile frame 110. In such an embodiment the forward cover portion 222 and the rearward cover portion 224 can be separate sterile cover portions, with the forward cover portion 222 being integrated with the sterile frame 110 and a rearward frame surface being configured to secure the rearward cover portion 224 to the touchscreen 50.

In an example for both single component and combination component embodiments, the forward cover portion 222 and the rearward cover portion 224 can be made of materials having different degrees of rigidity. In some cases the forward cover portion 222 and rearward cover portion 224 can be the same material. The forward cover portion 222 and/or rearward cover portion 224 can include a polymer material, such as polyester plastic, such as PET or TPU.

Figure 3:
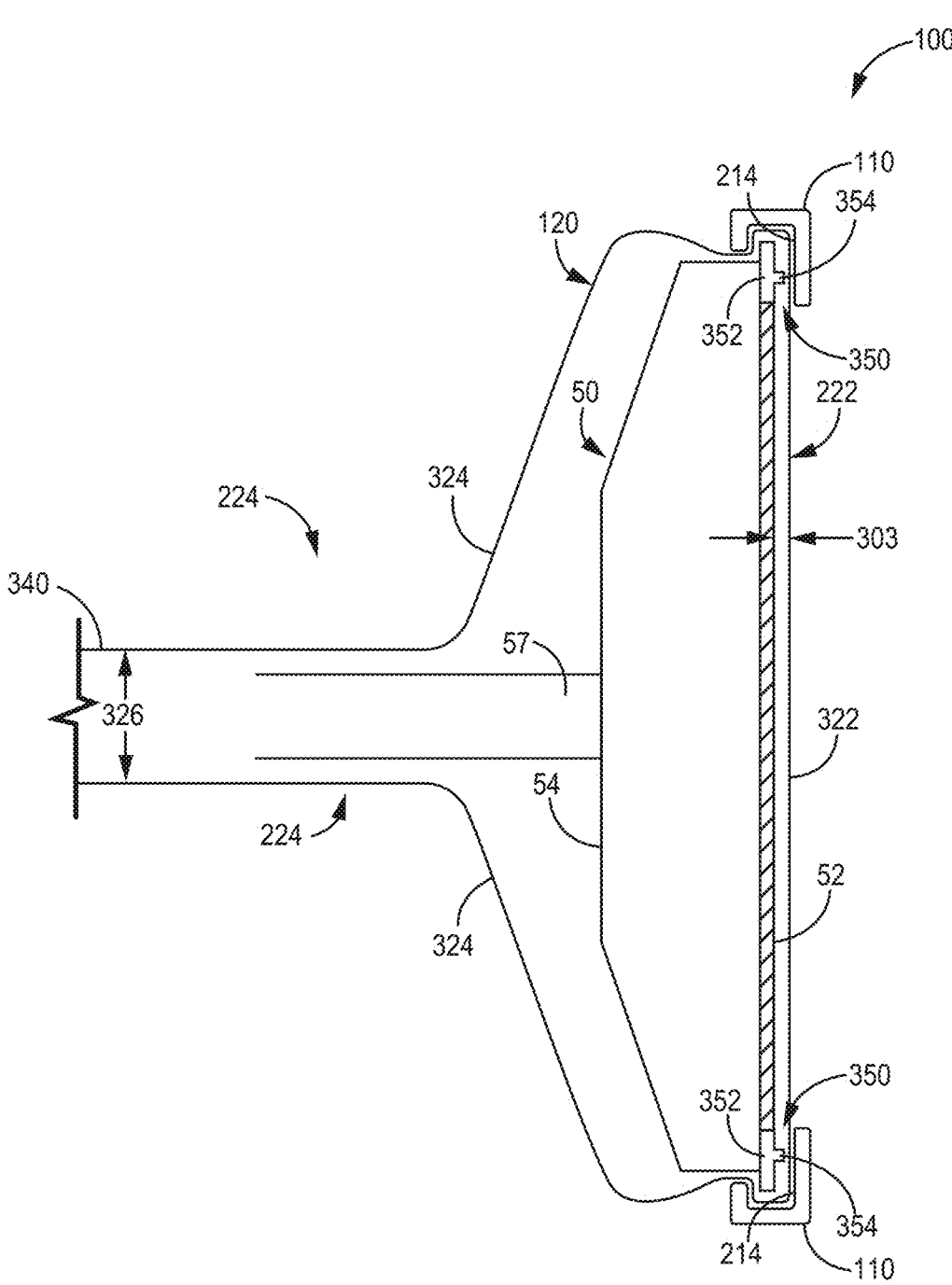
FIG. 3 is a side elevational view of the touchscreen cover assembly of FIG. 1 secured to a touchscreen.
Figure 5:
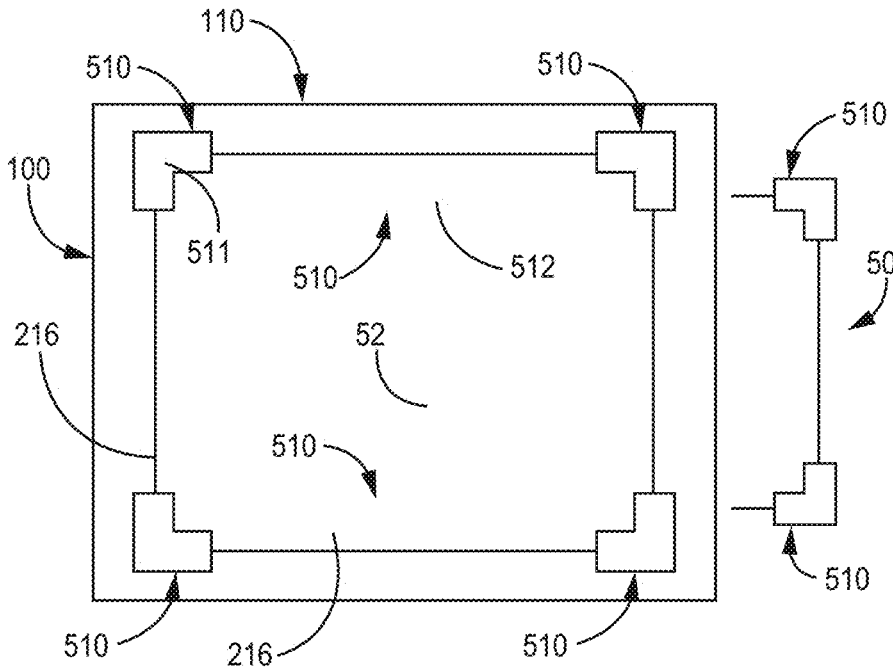
FIG. 5 is a plan view of a touchscreen and the touchscreen cover assembly of FIG. 1 with attachment members.
Figure 6:
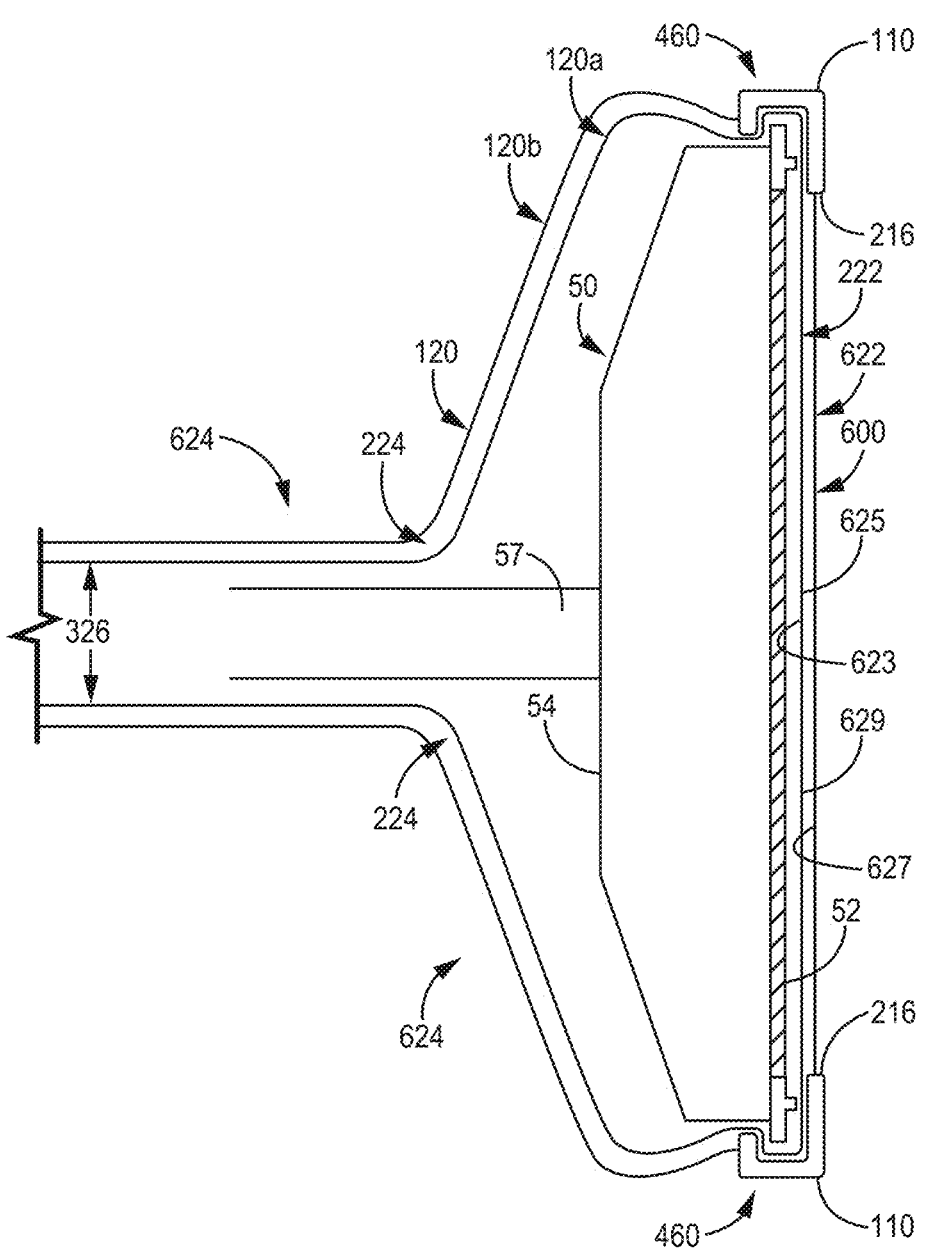
FIG. 6 is a side elevational view of another embodiment of a touchscreen cover assembly.
Figures 7A, 7B, 7C:
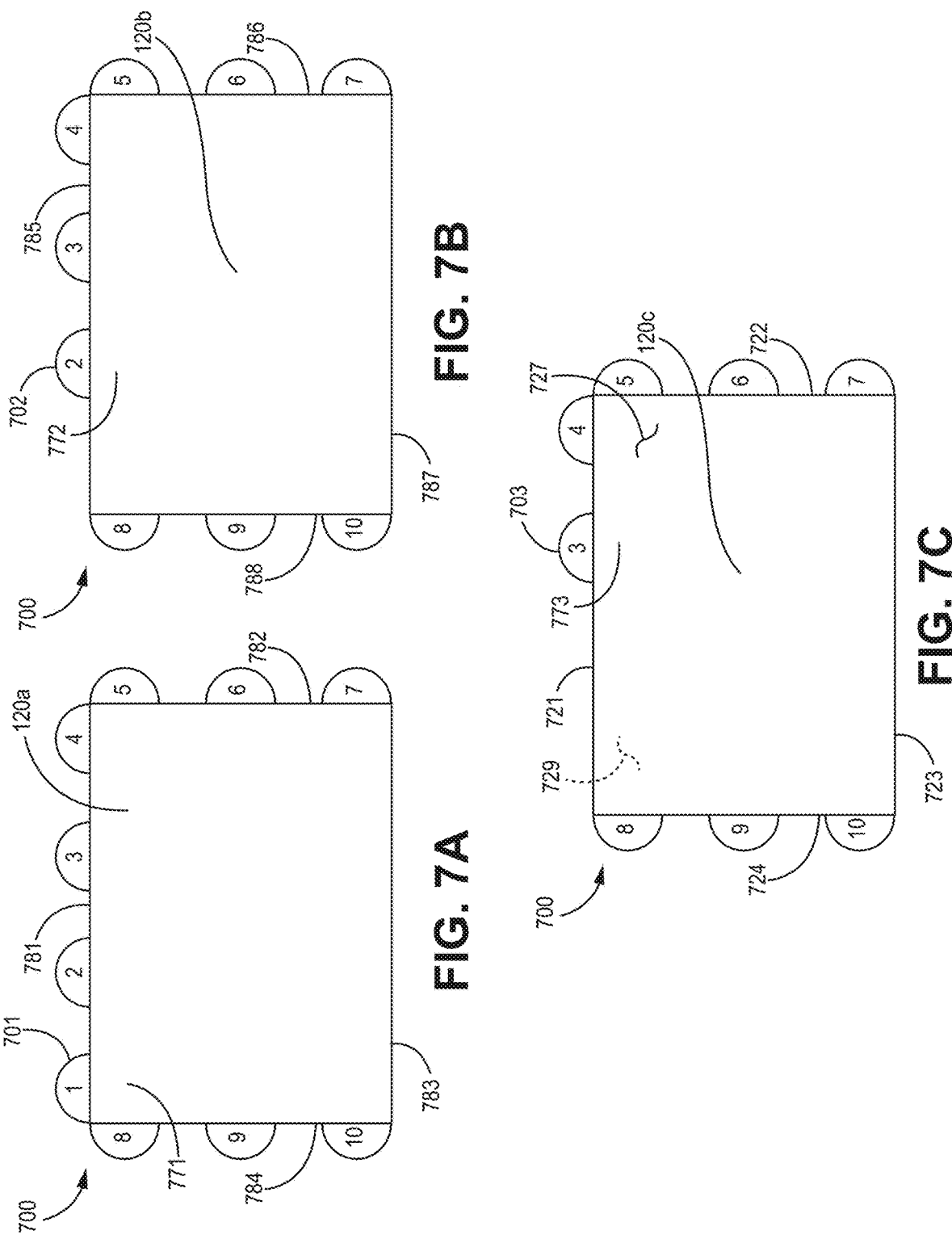
FIGS. 7A-7C show a sequence involving another embodiment of a touchscreen cover assembly including multiple sterile cover members.
Figure 8:
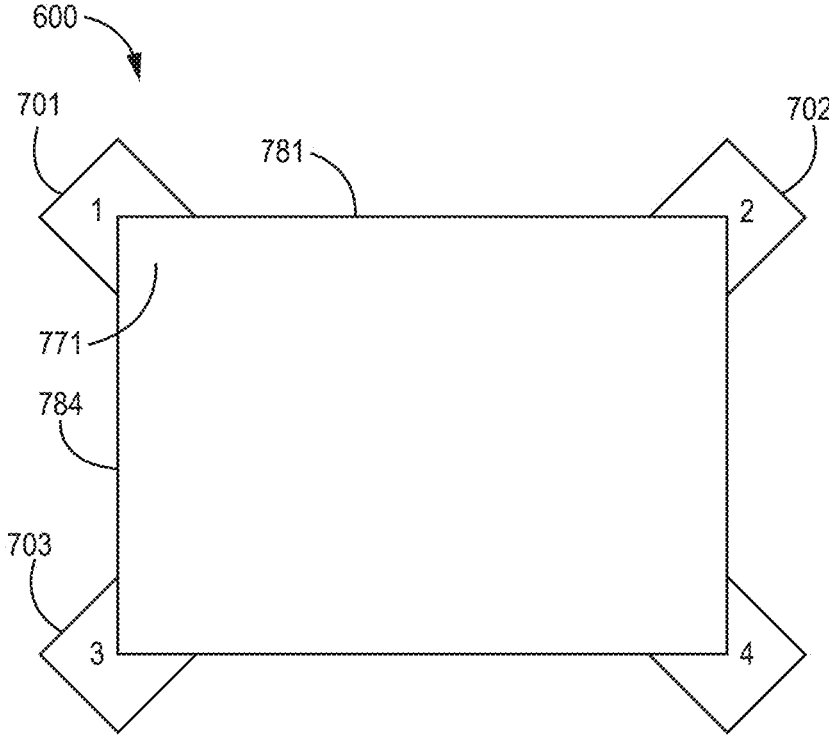
FIG. 8 is a plan view of a further tab arrangement embodiment of the touchscreen cover assembly of FIGS. 7A-7C where the tabs extend out from a different region of the touchscreen cover assembly.

As described throughout the remainder of the present disclosure, the touchscreen cover assembly 100 can include a single sterile cover member or multiple sterile cover members. FIGS. 3-5 illustrate embodiments of touchscreen cover assemblies having a single sterile cover member while FIGS. 6-8 illustrate embodiments of touchscreen cover assemblies having multiple sterile cover members.

FIG. 3 shows a side elevational view of the touchscreen cover assembly 100, with a single sterile cover member 120, secured to the touchscreen 50. In particular, in FIG. 3 the sterile cover member 120 of the touchscreen cover assembly 100 covers the touchscreen 50, including the housing 54 of the touchscreen 50, as well as a mounting mechanism 57 for the touchscreen 50.

As shown here, the forward cover portion 222 of the sterile cover member 120 can include a continuous cover segment 322 while the rearward cover portion 224 can include cover segments 324. As illustrated, the rearward cover portion 224 includes two cover segments 324 forming the rearward cover portion 224. The cover segments 324 can define a cover opening 326 between the cover segments 324. The sterile cover member 120 can be configured to be secured to the touchscreen 50 by the sterile frame 110 such that the cover segments 324 are positioned over the housing 54 of the touchscreen 50 and the cover opening 326 is opposite the user interface 52 of the touchscreen 50. In some such instances, in addition to be positioned over the housing 54, the cover segments 324 are positioned over a mounting mechanism 57 for the touchscreen 50 and the cover opening 326 is positioned around that mounting mechanism 57.

To assist in covering the touchscreen 50, including the housing 54, and mounting mechanism 57, the sterile cover member 120 can include a cover adjustment member 340. The cover adjustment member 340 can be configured, upon actuation, to reduce a space between the cover segments 324 and the housing 54 of the touchscreen 50. In certain cases, actuating the cover adjustment member 340 can occur before the touchscreen cover assembly 100 is secured to the touchscreen 50. In other cases, actuating the cover adjustment member 340 can occur after the touchscreen cover assembly 100 is secured to the touchscreen 50. Actuating the cover adjustment member 340, in some cases, can include pulling to tighten or close the sterile cover member 120 by bringing one or more of cover segments 324 toward the cover adjustment member 340. For example, the cover adjustment member 340 can comprise an elastic member or a non-elastic member, such as a drawstring.

In some embodiments, as shown in FIG. 3, the touchscreen cover assembly 100 can include a spacing tab 350 that creates a space 303 between the forward cover portion 222 and the user interface 52 of the touchscreen 50. In the illustrated example, two spacing tabs 350 are included at opposite ends of the touchscreen 50. The spacing tab 350 can be configured to be secured to the touchscreen 50 and to be positioned between the touchscreen 50 and the sterile cover member 120. The spacing tab 350 can include a base 352 and a lip 354. The base 352 can be configured to be secured to the touchscreen 50 (e.g., via an adhesive or removable fastener). The lip 354 can project out from the base 352 so as to create the space 303 between the forward cover portion 222 and the user interface 52 of the touchscreen 50. In some instances, the dimensions of the space 303 can be uniform across the user interface 52, and in other instances, the dimensions of the space 303 can be variable across the user interface 52. For example, the forward cover portion 222 can be between the lip 354 and the sterile frame 110 such that it is suspended over the touchscreen 50 at a substantially uniform distance from the user interface 52.

Figure 4A:
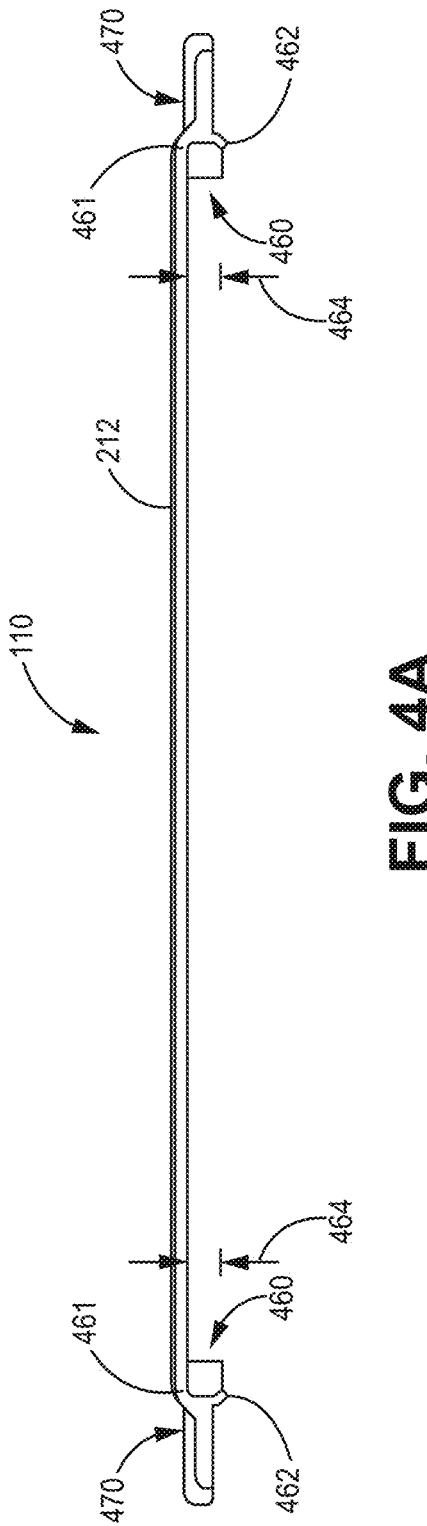
FIGS. 4A-4C show an embodiment of a sterile frame of the touchscreen cover assembly of FIG. 1.
Figure 4B:
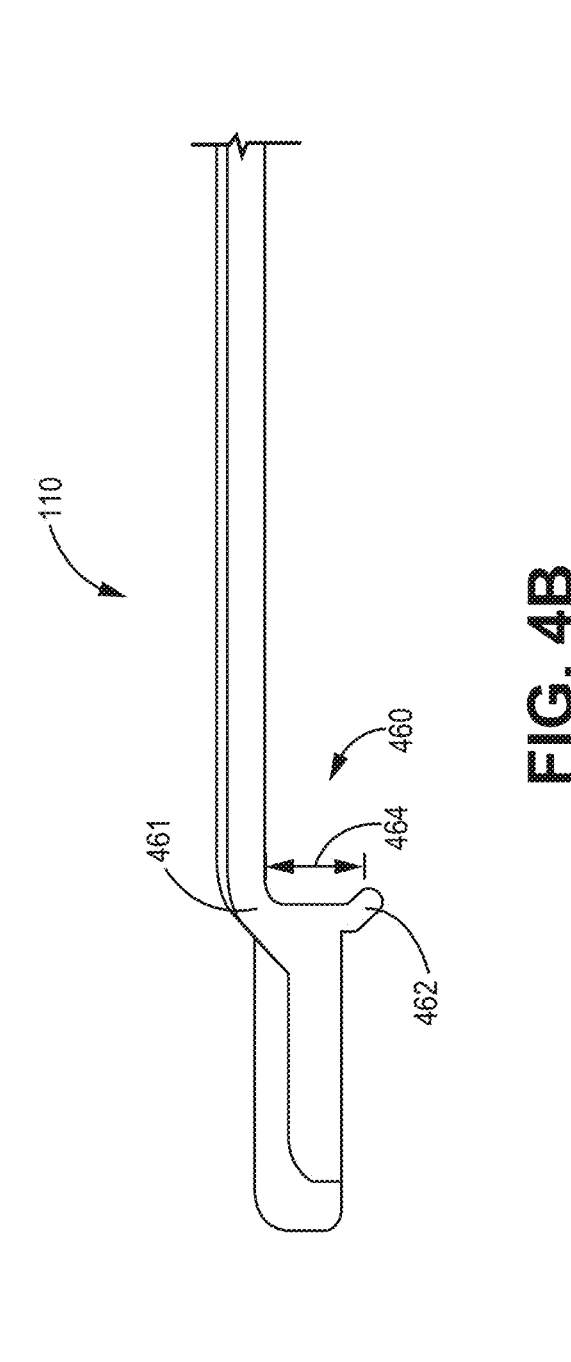
Figure 4C:
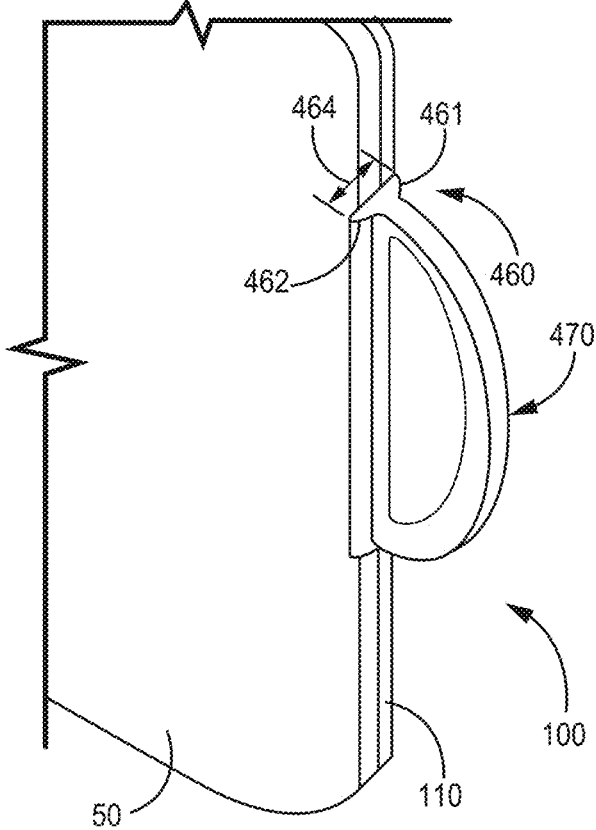

FIGS. 4A-4C show an embodiment of the sterile frame 110 of the touchscreen cover assembly 100. FIG. 4A is a side elevational view of the sterile frame 110, FIG. 4B is a close-up, side elevational view of a portion of the sterile frame 110 of FIG. 4A, and FIG. 4C is a close-up, perspective view of a portion of the sterile frame 110 of FIG. 4A with a handle 470 of the sterile frame 110 being secured to the touchscreen 50.

The sterile frame 110 can include one or more features that can facilitate securing the sterile cover member to the touchscreen 50. As illustrated here, the sterile frame 110 can include an adjustable securement member 460 and one or more handles 470. The sterile frame 110 is shown here with two handles 470. In the illustrated embodiment two adjustable securement members 460 are included at the sterile frame 110 at the same locations as the handles 470. The sterile frame 110 can include the one or more handles 470 and/or the accompanying one or more adjustable securement members 460 at any location along the sterile frame 110. For example, the sterile frame 110 can include the one or more handles 470 and/or the accompanying one or more adjustable securement members 460 at any location along a perimeter of the sterile frame 110. In one embodiment, the sterile frame 110 includes one handle 470 and one accompanying adjustable securement member 460, such as at a top perimeter surface of the sterile frame 110. In another embodiment, such as that shown in FIG. 4A, the sterile frame 110 includes two handles 470 and two accompanying adjustable securement members 460 at opposite perimeter surfaces of the sterile frame 110.

Each of the handle 470 and securement member 460 can facilitate securing the sterile frame 110 to the touchscreen. The sterile frame 110 can include the adjustable securement member 460, which can be configured to secure the sterile frame 110 to the touchscreen. Each of the handles 470 can extend outward from the sterile frame 110, for instance outward from the forward frame surface 212. In some instances, such as that shown here, a forward surface of the handle 470 can be offset from (e.g., forward or rearward of) forward frame surface 212. Each of the handles 470 can be sized to be ergonomically and comfortably gripped by a user's hand. By projecting out from the sterile frame 110, in certain examples, the handles 470 can be formed such that a user's hand gripping the handle 470 need not contact the sterile cover member and/or other portions of the touchscreen cover assembly in order to secure the sterile frame 110 to the touchscreen. In this way, such handles 470 can facilitate creating and maintaining a sterile interface between the touchscreen and the user.

The adjustable securement member 460 can include first and second securement arms 461, 462. The second securement arm 462 is spaced from the first securement arm 461. The first securement arm 461 and the second securement arm 462 can define a securement space 464 therebetween. The adjustable securement member 460 can take a variety of forms, including spring-loaded, levered, and resilient so as to be configured to vary the size of the securement space 464. According to some embodiments, the securement space 464 can be sized to accommodate certain size ranges common to touchscreens. The adjustable securement member 460 can be configured to be adjusted so as to change a size of the securement space 464 and thereby accommodate different sized touchscreens. In some such cases, adjusting the adjustable securement member 460 can include moving at least one of the first securement arm 461 and the second securement arm 462, thereby changing the size of the securement space 464. Such adjustments can be stepped (e.g., via a snap-fit of the securement arms at various locations) and/or continuous depending on the embodiment.

As shown in FIG. 4C, the securement space 464 can be configured to receive the touchscreen 50. As shown, once received, a portion of the touchscreen 50 can be positioned between the first securement arm 461 and the second securement arm 462. In certain cases, the adjustable securement member 460 can be adjusted to fit the touchscreen 50 before the touchscreen 50 is received within the securement space 464. In other cases, the adjustable securement member 460 can be adjusted to fit the touchscreen 50 as the touchscreen 50 is received within the securement space 464. The first securement arm 461 and the second securement arm 462 can be adjusted or fitted such that the touchscreen 50 can be received in the securement space 464 in a manner that prevents the touchscreen 50 from inadvertently falling out from the sterile frame 110. Thus, once the touchscreen 50 is received in the securement space 464, motion of the touchscreen cover assembly 100 relative to the touchscreen 50 can be limited.

As noted, each of the handles 470 can be aligned with an adjustable securement member 460. One handle 470 can be aligned along the sterile frame 110 with one adjustable securement member 460 and the other handle 470 can be aligned along the sterile frame 110 with the other adjustable securement member 460. This alignment can facilitate installing the sterile frame, and thus touchscreen cover assembly, at the touchscreen 50. For example, such an alignment can transfer an installation force applied to each handle 470 to the aligned adjustable securement member 460 so as to cause each adjustable securement member 460 to engage the sterile frame 110.

FIG. 5 shows a plan view of a touchscreen 50 and the touchscreen cover assembly 100 with attachment members 510. When included, the attachment members 510 can be configured to help secure the sterile frame 110 to the touchscreen 50. The particular type of attachment member 510 can vary amongst embodiments. For example, any combination of magnetic, adhesive, or other similar attachment members 510 can be used to removably secure the touchscreen cover assembly 100 to the touchscreen 50. The touchscreen cover assembly 100 can include any number of attachment members 510 to secure the sterile frame 110 at the touchscreen 50. The attachment members 510 can be positioned, for instance, at various locations along one or both of the sterile frame 110 and touchscreen 50 as suitable without interfering with operation of the user interface 52.

As one specific example, the attachment members 510 can be magnetic. In this example, the sterile frame 110 can include a first magnetic attachment member 511. The first magnetic attachment member 511 can be configured to attach to a second magnetic attachment member 512 that is at a surface of the touchscreen 50 (e.g., a surface of the touchscreen having the user interface 52 but at a location at that surface spaced from the user interface 52). The position of the first magnetic attachment member 511 on the sterile frame 110 can correspond to the position of the second magnetic attachment member 512 at the touchscreen 50 in a manner such that the interior opening 216 of the sterile frame 110 aligns with the user interface 52 of the touchscreen 50. The first magnetic attachment member 511 can be configured to magnetically attach to the second magnetic attachment member 512 to attach the sterile frame 110 to the touchscreen 50.

The touchscreen cover assembly embodiments illustrated to this point have included one sterile cover member. As noted previously, some embodiments of the touchscreen cover assembly 100 can include multiple sterile cover members.

FIG. 6 shows an embodiment of a touchscreen cover assembly 600 including multiple sterile cover members. In various embodiments, each of these multiple sterile cover members can cover the housing of the touchscreen as well as the mounting mechanism for the touchscreen.

FIG. 6 is a side elevational view of the touchscreen cover assembly 600. The touchscreen cover assembly 600 can include a first sterile cover member 120a and a second sterile cover member 120b together forming the sterile cover member 120. Each of the first sterile cover member 120a and the second sterile cover member 120b can have one or more (e.g., each) of the features described herein, and illustrated in the accompanying drawings, with respect to the sterile cover member 120. Though depicted spaced apart for simplicity, it should be understood that space between the first sterile cover member 120a and the second sterile cover member 120b can be nominal. As with the single sterile cover member embodiment, such a touchscreen cover assembly 600 can be configured to create a sterile interface between the touchscreen 50 and the user.

FIG. 6 shows features of the first sterile cover member 120a and the second sterile cover member 120b. As shown here, the second sterile cover member 120b can overlay the first sterile cover member 120a. The first sterile cover member 120a can include the forward cover portion 222 and the rearward cover portion 224. The second sterile cover member 120b can include a second forward cover portion 622, overlaying the forward cover portion 222 of the first sterile cover member 120a, and a second rearward cover portion 624, overlaying the rearward cover portion 224 of the first sterile cover member 120a. In this embodiment, the sterile cover member 120 can be configured to be secured to the touchscreen 50 by the sterile frame 110 such that the forward cover portion 222 of the first sterile cover member 120a is positioned between the second forward cover portion 622 and the user interface 52 of the touchscreen 50. Likewise, in this embodiment, the sterile cover member 120 can be configured to be secured to the touchscreen 50 by the sterile frame 110 such that the second forward cover portion 622 is positioned between the interior opening 216 and the forward cover portion 222 of the first sterile cover member 120a.

The first sterile cover member 120a and the second member 120b can be adhered to each other. In some cases, a portion, or all, of the first sterile cover member 120a can be adhered to a portion, or all, of the second sterile cover member 120b. In other cases, the first sterile cover member 120a can be adhered to the second sterile cover member 120b at selective locations of each sterile cover member. Some such cases can use adhesive positioned about the touchscreen cover assembly 600. In this way, the second sterile cover member 120b can be removably adhered to the first sterile cover member 120a such that when the second sterile cover member 120b is removed from the first sterile cover member 120a, the forward cover portion 222 of the first sterile cover member 120a is positioned between the interior opening 216 and the user interface 52 of the touchscreen 50 and the rearward cover portion 224 of the first sterile cover member 120a is positioned over the housing 54 of the touchscreen 50.

The first sterile cover member 120a and the second sterile cover member 120b can be secured to the touchscreen 50 using the sterile frame 110. The first sterile cover member 120a can have a first cover member rear surface 623 and a first cover member forward surface 625 opposite the first cover member rear surface 623. The second sterile cover member 120b can have a second cover member rear surface 627 and a second cover member forward surface 629 opposite the second cover member rear surface 627. The first cover member rear surface 623 can include a first adhesive that is configured to removably adhere the first sterile cover member 120a to the touchscreen 50. In one embodiment (e.g., as depicted in FIGS. 7A-7C), the first adhesive can be configured to removably adhere the first sterile cover member 120a to the second sterile cover member 120b. The second cover member rear surface 627 can include a second adhesive removably adhering the second sterile cover member 120b to the first cover member forward surface 625. In such embodiment, the second adhesive can be configured to removably adhere the second sterile cover member 120b to another (e.g., third) sterile cover member. Thus, when the first adhesive adheres the first sterile cover member 120a to the touchscreen 50, the first adhesive and the second adhesive can be configured to allow the second sterile cover member 120b to be removed from the first sterile cover member 120a while continuing to adhere the first sterile cover member 120a to the touchscreen 50.

Adhered together first and second sterile cover member 120a, 120b can cover the touchscreen 50 and the mounting mechanism 57 of the touchscreen 50, as illustrated in the example of FIG. 6. Namely, the first sterile cover member 120a can include the first cover member forward cover portion 222 and the first cover member rearward cover portion 224. The second sterile cover member 120b can include the second cover member forward cover portion 622 and the second cover member rearward cover portion 624. The first adhesive can be configured to removably adhere the first cover member forward cover portion 222 to the user interface 52 of the touchscreen 50 such that the second cover member forward cover portion 622 is positionable over the user interface 52 and each of the first cover member rearward cover portion 224 and the second cover member rearward cover portion 624 is positionable over the housing 54 of the touchscreen 50. In some such embodiments, each of the first sterile cover member 120a and the second sterile cover member 120b can be configured such that each of the first cover member rearward cover portion 224 and the second cover member rearward cover portion 624 is positionable over the housing 54 of the touchscreen 50 at a surface of the touchscreen 50 different than a surface of the touchscreen 50 having the user interface 52.

FIGS. 7A-7C show a sequence involving another embodiment of a touchscreen cover assembly 700 including multiple sterile cover members. FIG. 7A is a plan view of the touchscreen cover assembly 700 having multiple sterile cover members each with a tab. FIG. 7B is a plan view of the touchscreen cover assembly 700 after a first sterile cover member, present in FIG. 7A, has been removed to reveal a second sterile cover member. And, FIG. 7C is a plan view of the touchscreen cover assembly 700 after the second sterile cover member, present in FIG. 7B, has been removed to reveal a third sterile cover member.

In the sequence shown here with respect to the touchscreen cover assembly 700, individual sterile cover members can be removed from other sterile cover members while maintaining the sterility of the remaining sterile cover members in the assembly 700. The sterile cover members included in the assembly 700, including the sterile cover members 120a, 120b, 120c, can each have one or more (e.g., each) of the features described herein, and illustrated in the accompanying drawings, with respect to the sterile cover member 120 (including the sterile cover members 120a, 120b). In some embodiments, the sterile frame, illustrated and described elsewhere herein, can serve as a base member upon which the sterile cover members included in the assembly 700, including the sterile cover members 120a, 120b, 120c, are stacked upon. Thus, in such embodiments, the sterile frame can serve as a base, one cover member 120c can be laid onto the sterile frame base, another cover member 120b can be laid onto the cover member 120c, and a further cover member 120a can be laid onto the cover member 120b.

As shown in FIG. 7A, the first sterile cover member 120a can include a first tab 701 extending out from the first sterile cover member 120a at a first region 771 of the touchscreen cover assembly 700. The first tab 701 can take a variety of forms, including varying in shape and size. As shown in the embodiment of FIG. 7A, the first tab 701 can include identification mark, such as the numeral one, indicating that it is a first tab to be removed from the assembly 700. The first region 771 can be at a perimeter of side of the first sterile cover member 120a or any part of the first sterile cover member 120a.

The first tab 701 can be used to remove the first sterile cover member 120a from the assembly 700, for instance once a first medical procedure has ended and prior to a subsequent, second medical procedure beginning. FIG. 7B shows the assembly 700 after the first sterile cover member 120a has been removed such that the second sterile cover member 120b is now exposed as the outermost sterile cover member. By covering the second sterile cover member 120b with the first sterile cover member 120a, sterility of the second sterile cover member 120b can be maintained while the first sterile cover member 120a is present. The second sterile cover member 120b can include a second tab 702 extending out from the second sterile cover member 120b at a second region 772 of the touchscreen cover assembly 700 spaced apart from the first region 771. For instance, the second region 772 can be positioned such that it does not overlap with the first region 771. This may result in the first and second tabs 701, 702 being spaced apart a sufficient distance such that the second tab 702 is not touched when the first tab 701 is gripped to remove the first sterile cover member 120a. Such an arrangement of the first tab 701 and the second tab 702 can allow the user and the second sterile cover member 120b to remain sterile while the first cover member 120a is removed.

With reference to FIGS. 7A and 7B, the second tab 702 can be positioned relative to the position of the first tab 701. The first sterile cover member 120a can include a first cover member first side 781, a first cover member second side 782, a first cover member third side 783, and a first cover member fourth side 784. Likewise, the second sterile cover member 120b can include a second cover member first side 785 aligned with the first cover member first side 781, a second cover member second side 786 aligned with the first cover member second side 782, a second cover member third side 787 aligned with the first cover member third side 783, and a second cover member fourth side 788 aligned with the first cover member fourth side 784. The first cover member first side 781 can include the first region 771, and the second cover member second side 786 can include the second region 772.

The second tab 702 can be used to remove the second sterile cover member 120b from the assembly 700, for instance once a second medical procedure has ended and prior to a subsequent, third medical procedure beginning. FIG. 7C shows the touchscreen cover assembly 700 after the second sterile cover member 120b has been removed such that the third sterile cover member 120c is now exposed as the outermost sterile cover member. By covering the third sterile cover member 120c with the second sterile cover member 120b, sterility of the third sterile cover member 120c can be maintained while the second cover member 120b is present. The third sterile cover member 120c can include a third tab 703 extending out from the third sterile cover member 120c at a third region 773 of the touchscreen cover assembly 700 spaced apart from the first and second regions 771, 772. For instance, the third region 773 can be positioned such that it does not overlap with the first or second region 771, 772. This may result in the third tab 703 being spaced apart from each of the first and second tabs 701, 702 a sufficient distance such that the third tab 703 is not touched when the first or second tab 701, 702 is gripped to remove the first sterile cover member 120a and second sterile cover member 120b. Such an arrangement of the first, second, and third tabs 701, 702, 703 can allow the user and the third sterile cover member 120c to remain sterile while the first and second cover member 120a, 120b are removed.

The third sterile cover member 120c can be removably adhered to the second sterile cover member 120b and, when other, additional sterile cover members are present in the assembly 700, the third sterile cover member 120c can be removable adhered to the adjacent, underlying sterile cover member. When the third adhesive removably adheres the third sterile cover member 120c to an underlying sterile cover member (or the touchscreen), each of the first, second, and third adhesive can be configured to allow the first sterile cover member 120a to be removed from the second sterile cover member 120b while adhering the second sterile cover member 120b to the third sterile cover member 120c and the third sterile cover member 120c to the underlying sterile cover member (or touchscreen).

With reference to FIGS. 7A-7C, the third tab 703 can be positioned relative to the positions of the first and second tabs 701, 702. The third sterile cover member 120c can include a third cover member first side 721 aligned with the second cover member first side 785, a third cover member second side 722 aligned with the second cover member second side 786, a third cover member third side 723 aligned with the second cover member third side 787, and a third cover member fourth side 724 aligned with the second cover member fourth side 788. In the illustrated embodiment, the third cover member third side 723 can include the third region 773 with the third tab 703.

In some embodiments, the touchscreen (e.g., the touchscreen 50) can be configured to facilitate user inputs at the touchscreen while a touchscreen cover assembly (e.g., the touchscreen cover assembly 100, the touchscreen cover assembly 600, the touchscreen cover assembly 700) is at the touchscreen. For example, the touchscreen can be programmed to adjust the touchscreen's sensitivity to user touch inputs as a function of the touchscreen cover assembly at the touchscreen at a given point in time.

Computer executable instructions can be stored at a non-transitory computer readable medium at the touchscreen and executed by a programmable processor at the touchscreen to adjust the touchscreen's sensitivity to user touch inputs as a function of the touchscreen cover assembly at the touchscreen. For instance, the computer executable instructions can be executed to make the touchscreen more sensitive to user touch inputs when a touchscreen cover assembly is present at the touchscreen. In some such instances, the extent to which the touchscreen's sensitivity is increased to be more sensitive to user touch inputs can vary depending on the particular embodiment of the cover assembly present at the touchscreen. For example, an input can be provided at the touchscreen corresponding to a type of cover assembly present at the touchscreen and the computer executable instructions can be executed using the input type of cover assembly to increase touchscreen's sensitivity to user touch inputs to an extent suitable for the input type of cover assembly. Depending on the input type of cover assembly, the extent to which the touchscreen's sensitivity is increased can vary.

In instances where the cover assembly embodiment includes multiple cover members, the computer executable instructions can be executed at the touchscreen to account for the multiple cover members. For example, the computer executable instructions can initially be executed at the touchscreen using the input type of cover assembly to increase touchscreen's sensitivity to user touch inputs to an extent suitable for the input type of cover assembly. In some cases, the input type of cover assembly can specify a number of cover members included at the touchscreen. Then, as one cover member is removed, the computer executable instructions can be executed at the touchscreen to reduce the touchscreen's sensitivity to user touch inputs to an extent suitable to account for the removed cover member and, thus, resulting reduced thickness of the cover assembly now present at the touchscreen. Similarly, as another cover member is removed, the computer executable instructions can be executed at the touchscreen to further reduce the touchscreen's sensitivity to user touch inputs to a further extent suitable to account for the second removed cover member and, thus, the further resulting reduced thickness of the cover assembly now present at the touchscreen.

In one embodiment, the touchscreen can detect when a cover member is removed from the cover assembly present at the touchscreen and thereby execute the computer executable instructions, in an automated manner, to adjust (e.g., reduce) the touchscreen's sensitivity to user touch inputs. For example, the cover members of the cover assembly can each include a cover presence facilitating feature and the touchscreen can include a cover presence reading feature. The touchscreen can be configured to use the cover presence reading feature to detect the cover presence facilitating feature of each cover member at the cover assembly at the touchscreen. In this way, the touchscreen can detect the number of cover members present and utilize this information to adjust the touchscreen's sensitivity to user touch inputs as described above, including, for instance, initially increasing sensitivity as a function of the number of cover members present and then sequentially reducing sensitivity each time cover member removal is detected. As one example, the presence facilitating feature at each cover member can be a RFID emitter and the presence reading feature at the touchscreen can be a RFID receiver. As another example, the presence facilitating feature at each cover member can be a magnetic component and the presence reading feature at the touchscreen can be a magnetic field sensor. Various other types of presence facilitating features and presence reading features can be utilized to identify the number of cover members present at the touchscreen at a given point in time.

FIG. 8 shows a plan view of a further tab arrangement embodiment of the touchscreen cover assembly 700. In this illustrated tab arrangement, the tabs 701, 702, 703 each extend out from different regions of the assembly 700. For example, in such an arrangement, any of the first region 771, the second region, and the third region can span portions of two sides of the respective sterile cover member. As illustrated in FIG. 8, the first region 771 can include the first cover member first side 781 and the first cover member fourth side 784 such that the first tab 701 is at both of the first cover member first side 781 and the first cover member fourth side 784. Here, the second region can include the second cover member first side and the second cover member second side and the third region can include the third cover member second side and the third cover member third side.

Figure 9:
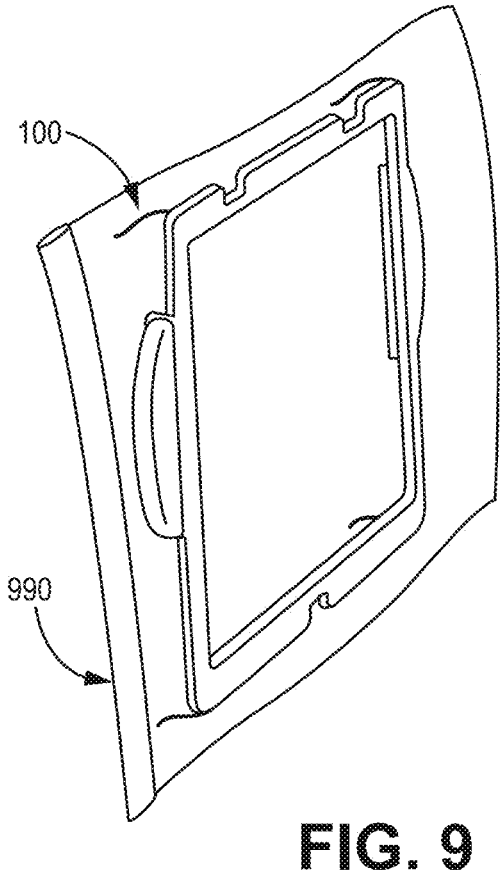
FIG. 9 is a perspective view of an embodiment of a sterile packaging enclosing a touchscreen cover assembly embodiment.

FIG. 9 shows a perspective view of an embodiment of a sterile packaging 990 enclosing the touchscreen cover assembly 100. The touchscreen cover assembly 100, enclosed in the sterile packaging 990, can have one or more (e.g., each) of the features described herein, and illustrated in the accompanying drawings, with respect to the various touchscreen cover assembly embodiments.

The sterile packaging 990 can enclose the touchscreen cover assembly 100 such that the touchscreen cover assembly 100 is sealed with the exterior environment until the sterile packaging 990 is opened. The sterile packaging 990 can be sealed such that a touchscreen cover assembly 100 that has been sterilized remains sterilized as long as it is sealed within the sterile packaging 990. The sterile packaging 990 can be large enough (e.g., sized just larger than the touchscreen cover assembly 100) to safely receive and envelope the touchscreen cover assembly 100.

Figure 10:
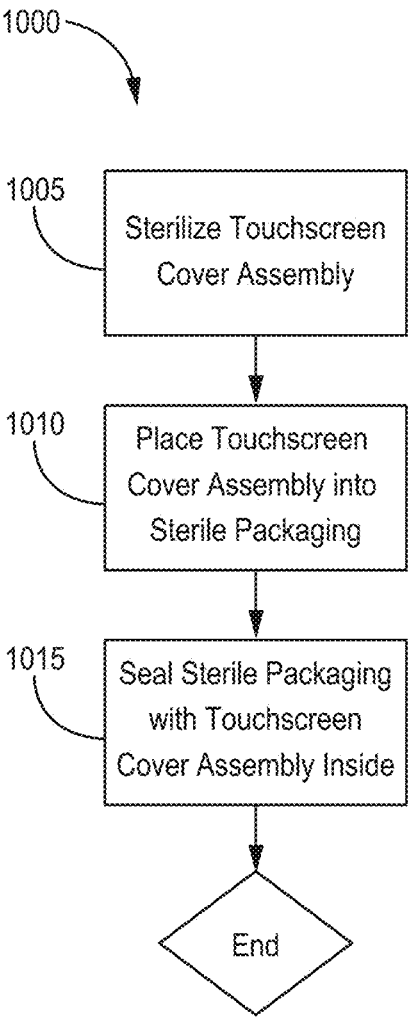
FIG. 10 is a flowchart illustrating an embodiment of a method of packaging an embodiment of a touchscreen cover assembly in a sterile packaging.

FIG. 10 shows a flowchart illustrating an embodiment of a method 1000 of packaging a touchscreen cover assembly in a sterile packaging. The touchscreen cover assembly in the method 1000 can have one or more (e.g., each) of the features described herein, and illustrated in the accompanying drawings, with respect to the various touchscreen cover assembly embodiments.

At step 1005, the touchscreen cover assembly can be sterilized. Sterilization methods can include a variety of sterilization techniques, including steam under pressure and/ or radiation.

At step 1010, the touchscreen cover assembly can be placed into packaging. The packaging can be in various forms. As one example, the packaging can be the sterile packaging described elsewhere herein configured for sealing the touchscreen cover assembly from an exterior environment.

At step 1015, the sterile packaging can be sealed with the touchscreen cover assembly inside of the interior volume of the sterile packaging. Sealing the sterile packaging can include vacuum sealing or otherwise sealing either with single-use or multiple-use seals.

Figure 11:
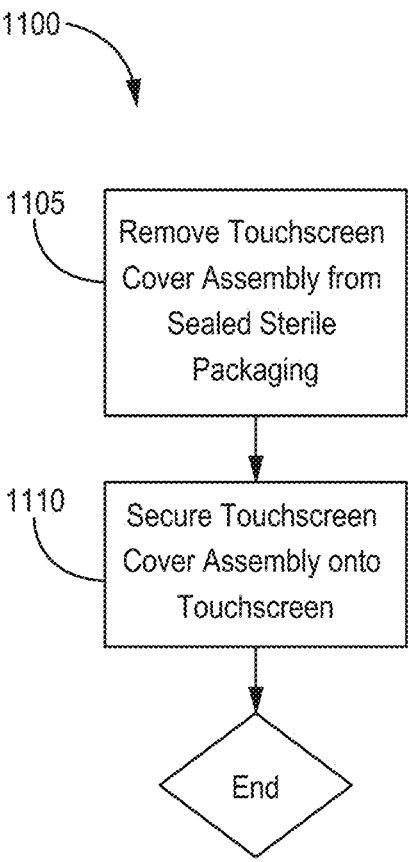
FIG. 11 is a flowchart illustrating an embodiment of a method of securing an embodiment of a touchscreen cover assembly at a touchscreen.

FIG. 11 shows a flowchart illustrating an embodiment of a method 1100 of securing a touchscreen cover assembly at a touchscreen so as to create a sterile interface between a touchscreen and a user. The touchscreen cover assembly in the method 1100 can have one or more (e.g., each) of the features described herein, and illustrated in the accompanying drawings, with respect to the various touchscreen cover assembly embodiments.

At step 1105, the touchscreen cover assembly can be removed from a sterile packaging. For instance, the sterile packaging may be sealed and removing the touchscreen cover assembly from the sterile packaging can include breaking the sterile packaging's seal to its interior volume.

At step 1110, the touchscreen cover assembly can be secured onto a touchscreen. For example, the touchscreen cover assembly can be secured to the touchscreen by simultaneously pressing the sterile frame against the touchscreen using the first and/or second handles until the adjustable securement member has received the touchscreen in the securement space. In other examples, a user can alternatingly press the first handle against the touchscreen until the first adjustable securement member has received the touchscreen in its securement space and then press the second handle against the touchscreen until the second adjustable securement member has received the touchscreen in its securement space. Where the touchscreen sterile cover member includes one or more magnetic attachment members, a user can bring the touchscreen cover assembly into proximity with the touchscreen such that a magnetic attachment member of the sterile frame and/or sterile cover member can be attracted to corresponding magnetic attachment member at the touchscreen.

In some examples, at step 1110, before or after pressing the sterile frame against the touchscreen or bringing the sterile frame into proximity to the touchscreen, a user can position the sterile cover member over a housing of the touchscreen and/or over the mounting mechanism, the connected cabling, or the control line. A user can, as appropriate, adjust the size of the adjustable securement member so as to change a size of the securement space to receive the touchscreen onto which the touchscreen cover assembly will be installed. The user can, as appropriate, actuate the cover adjustment member to thereby reduce the space between cover segments in the housing of the touchscreen. Each of adjusting the adjustable securement member and actuating the cover adjustment member can occur before or after seen cover assembly to the touchscreen.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A touchscreen cover assembly configured to create a sterile interface between a touchscreen and a user, the touchscreen cover assembly comprising:

a sterile frame including a forward frame surface and a rearward frame surface opposite the forward frame surface, the sterile frame defining an interior opening, wherein the sterile frame is configured to be secured to the touchscreen such that the rearward frame surface faces the touchscreen and the interior opening is aligned with a user interface of the touchscreen; and a sterile cover member including a forward cover portion and a rearward cover portion, the forward cover portion integrated with the sterile frame and extending in a plane across the interior opening of the sterile frame, wherein the sterile cover member is configured to be secured to the touchscreen by the sterile frame such that the forward cover portion is positioned between the interior opening and the user interface of the touchscreen and the rearward cover portion is positioned over a housing of the touchscreen, wherein the sterile frame includes at least one adjustable securement member configured to secure the sterile frame to the touchscreen, the at least one adjustable securement member including a first adjustable securement member having a first securement arm and a second securement arm spaced from the first securement arm, the first securement arm and the second securement arm defining a first securement space therebetween configured to receive the touchscreen, wherein the first adjustable securement member is configured to be adjusted so as to change a size of the first securement space, wherein the sterile frame includes at least one handle, each at least one handle extending outward from a respective one of the at least one adjustable securement member in a direction parallel to the touchscreen, wherein each at least one handle includes a forward handle surface facing a common direction with the forward frame surface, wherein the sterile frame includes at least one first removable handling interface and the sterile cover member includes at least one second removable handling interface, each at least one first removable handling interface disposed on the forward frame surface and the forward handle surface of a respective one of the at least one handle, each at least one first and second removable handling interfaces configured to be used as contact points for the user while positioning the touchscreen cover assembly at the touchscreen, and configured to be removed from the sterile frame and sterile cover member respectively without contacting either the sterile frame or the sterile cover member.

2. The assembly of claim 1, wherein the sterile cover member is configured to be secured to the touchscreen by the sterile frame such that the rearward cover portion is positioned over the housing of the touchscreen at a first surface of the touchscreen different than a second surface of the touchscreen having the user interface.

3. The assembly of claim 1, wherein the forward cover portion includes a continuous cover segment, and wherein the rearward cover portion includes cover segments defining a cover opening therebetween, and wherein the sterile cover member is configured to be secured to the touchscreen by the sterile frame such that the cover segments are positioned over the housing of the touchscreen and the cover opening is opposite the user interface of the touchscreen.

4. The assembly of claim 3, wherein the sterile cover member is configured to be secured to the touchscreen by the sterile frame such that the cover segments are positioned over a mounting mechanism for the touchscreen and the cover opening is positioned around the mounting mechanism for the touchscreen.

5. The assembly of claim 3, further comprising:
a cover adjustment member configured, upon actuation, to reduce a space between the cover segments and the housing of the touchscreen.

6. The assembly of claim 1, wherein the forward cover portion and the rearward cover portion are separate sterile cover portions, wherein the rearward frame surface is configured to secure the rearward cover portion to the touchscreen.

7. The assembly of claim 1, wherein the forward cover portion and the rearward cover portion are integrated to form a single piece sterile cover member.

8. The assembly of claim 1, further comprising:
a spacing tab configured to be secured to the touchscreen and be positioned between the touchscreen and the sterile cover member, the spacing tab including a base configured to be secured to the touchscreen and a lip projecting out from the base so as to create a space between the forward cover portion and the user interface of the touchscreen.

9. The assembly of claim 1, wherein the at least one adjustable securement member includes a second adjustable securement member having a third securement arm and a fourth securement arm spaced from the third securement arm, the third securement arm and the fourth securement arm defining a second securement space therebetween configured to receive the touchscreen, wherein the second adjustable securement member is configured to be adjusted so as to change a size of the second securement space,
the at least one handle includes a first handle and a second handle, wherein the first handle extends outward from the first adjustable securement member in a direction parallel to the touchscreen and the second handle extends outward from the second adjustable securement member in a direction parallel to the touchscreen.

10. The assembly of claim 1, wherein the sterile cover member includes a first sterile cover member and a second sterile cover member overlaying the first sterile cover member, wherein the first sterile cover member includes the forward cover portion and the rearward cover portion, wherein the second sterile cover member includes a second forward cover portion overlaying the forward cover portion of the first sterile cover member and a second rearward cover portion overlaying the rearward cover portion of the first sterile cover member, wherein the sterile cover member is configured to be secured to the touchscreen by the sterile frame such that the forward cover portion of the first sterile cover member is positioned between the second forward cover portion and the user interface of the touchscreen and the second forward cover portion is positioned between the interior opening and the forward cover portion of the first sterile cover member.

11. The assembly of claim 10, wherein the second sterile cover member is removably adhered to the first sterile cover member such that when the second sterile cover member is removed from the first sterile cover member the forward cover portion of the first sterile cover member is positioned between the interior opening and the user interface of the touchscreen and the rearward cover portion of the first sterile cover member is positioned over the housing of the touchscreen.

12. The assembly of claim 1, further comprising:
a first magnetic attachment member at the sterile frame, wherein the first magnetic attachment member is configured to magnetically attach to a second magnetic attachment member at the touchscreen to attach the sterile frame to the touchscreen.

13. The assembly of claim 1, wherein the at least one first removable handling interface is in the form of a tab.

14. The assembly of claim 1, wherein the at least one second removable handling interface is in the form of a pull string.

15. A touchscreen cover assembly configured to create a sterile interface between a touchscreen and a sterile user, the touchscreen cover assembly comprising:
a sterile frame including a forward frame surface and a rearward frame surface opposite the forward frame surface, the sterile frame defining an interior opening, wherein the sterile frame is configured to be secured to the touchscreen such that the rearward frame surface faces the touchscreen and the interior opening is aligned with a user interface of the touchscreen; and
a sterile cover member including a forward cover portion and a rearward cover portion, the forward cover portion integrated with the sterile frame and extending in a plane across the interior opening of the sterile frame, wherein the sterile cover member is configured to be secured to the touchscreen by the sterile frame such that the forward cover portion is positioned between the interior opening and the user interface of the touchscreen and the rearward cover portion is positioned over a housing of the touchscreen,
wherein the sterile frame includes at least one adjustable securement member configured to secure the sterile frame to the touchscreen, the at least one adjustable securement member including a first adjustable securement member having a first securement arm and a second securement arm spaced from the first securement arm, the first securement arm and the second securement arm defining a first securement space therebetween configured to receive the touchscreen, wherein the first adjustable securement member is configured to be adjusted so as to change a size of the first securement space, wherein the sterile frame includes at least one first-handle, each at least one handle extending outward from a respective one of the at least one adjustable securement member in a direction parallel to the touchscreen, wherein each at least one handle includes a forward handle surface facing a common direction with the forward frame surface, wherein the sterile frame includes at least one first removable handling interface and the sterile cover member includes at least one second removable handling interface, each at least one said first removable handling interface disposed on the forward frame surface and the forward handle surface of a respective one of the at least one handle, each at least one first and second removable handling interfaces configured to be gripped by a non-sterile user to position the touchscreen cover assembly at the touchscreen, and to be removed by the non-sterile user from the touchscreen cover assembly after the sterile frame is secured to the touchscreen and before the sterile user interacts with the touchscreen.

16. The assembly of claim 15, further comprising:

a spacing tab configured to be secured to the touchscreen and be positioned between the touchscreen and the sterile cover member, the spacing tab including a base configured to be secured to the touchscreen and a lip projecting out from the base so as to create a space between the forward cover portion and the user interface of the touchscreen.

17. The assembly of claim 15, wherein the at least one first removable handling interface is in the form of a tab.

* * * * *